United States Patent [19]

Marks et al.

[11] 4,364,870

[45] Dec. 21, 1982

[54] ONE-STEP SYNTHESES OF URANIUM HEXAMETHOXIDE AND MIXED METHOXY URANIUM (VI) FLUORIDES FROM URANIUM HEXAFLUORIDE AND TWO-STEP SYNTHESIS OF URANIUM HEXAMETHOXIDE FROM URANIUM TETRACHLORIDE

[75] Inventors: Tobin J. Marks; Edward A. Cuellar, both of Evanston, Ill.; Steven S. Miller, New York, N.Y.; Eric Weitz, Evanston, Ill.

[73] Assignee: Northwestern University, Evanston, Ill.

[21] Appl. No.: 137,440

[22] Filed: May 5, 1980

[51] Int. Cl.$^3$ .......................... C07F 5/00; B01J 19/08
[52] U.S. Cl. .......................... 260/429.1; 204/157.1 R; 204/DIG. 11; 260/429.2
[58] Field of Search .......................... 260/429.1, 429.2

[56] References Cited

U.S. PATENT DOCUMENTS

| | | | |
|---|---|---|---|
| 2,727,000 | 12/1955 | Drewer et al. | 260/429.1 |
| 2,735,857 | 2/1956 | Gilman et al. | 260/429.1 |
| 3,356,703 | 12/1967 | Mazdiyashi et al. | 260/429.1 |
| 3,718,677 | 2/1973 | Pitts, Jr. | 260/429.1 |
| 3,754,011 | 8/1973 | Hoch | 260/429.1 |
| 4,097,384 | 6/1978 | Coleman et al. | 250/527 |

OTHER PUBLICATIONS

Jones, R. C., et al., J.A.C.S., vol. 78, pp. 6027–6029, 6030–6032 (Dec. 5, 1956).
Jones, R. C., et al., J.A.C.S., vol. 78, No. 17, pp. 4285–4290, (Sep. 5, 1956).
Bradley, D. C., et al., J. Inorg., Nucl. Chem., vol. 4, pp. 279–282, (1957).
Selbin, Joel, et al., Chem. Rev., vol. 69, pp. 657–671, (1969).

*Primary Examiner*—Teddy S. Gron
*Attorney, Agent, or Firm*—Michael G. Berkman

[57] ABSTRACT

The invention relates to an improved method for synthesizing uranium hexamethoxide and new mixed methoxy uranium (VI) fluorides from uranium hexafluorides. Irradiation of the products of the invention in the vapor phase, with a pulsed $CO_2$ gas laser leads to enrichment in the U-235 content of the isotopic mixture containing U-235 and U-238, the degree of enrichment depending upon the laser frequency employed.

3 Claims, No Drawings

ONE-STEP SYNTHESES OF URANIUM HEXAMETHOXIDE AND MIXED METHOXY URANIUM (VI) FLUORIDES FROM URANIUM HEXAFLUORIDE AND TWO-STEP SYNTHESIS OF URANIUM HEXAMETHOXIDE FROM URANIUM TETRACHLORIDE

FIELD OF THE INVENTION

Uranium isotope separation is a very important problem in today's society. Uranium fueled reactors provide, at present, about 10% of the total U.S. electrical power. At least for the short term, this percentage will continue to increase. Thus, cheap uranium isotope separation (for the production of $^{235}U$ enriched fissionable fuel) would be of tremendous economic value. It has been estimated that at least 50 billion dollars will be spent on uranium fuel production in this country between now and the year 2000.

The currently used process for uranium enrichment in the U.S., gaseous diffusion, is 35 years old, is very equipment and power intensive, and has been improved very little since the 1940's. With the advent of laser isotope separation it was realized that efficient laser separation of uranium isotopes was in principle possible. The approach taken by most groups working in the field has been to try to use uranium hexafluoride ($UF_6$) as the parent compound for separation. The major advantage of this compound is that it has been used for over 35 years in the gaseous diffusion process. Thus, its properties are well known, synthetic routes have been well worked out, and machinery and equipment are available that are compatible with its highly corrosive and toxic nature.

However, there is no reason to believe that the best compound for isotope separation via gaseous diffusion will be the best compound for isotope separation via multiphoton laser processes. In fact, there are significant problems with the use of $UF_6$ in a laser isotope separation process. $UF_6$ does not absorb in the $10\mu$ region of the infrared, which is the spectral region of operation of the carbon dioxide laser, the laser which to date has been most widely utilized for isotope separation. This use is due to the high power, high efficiency, and low cost of the carbon dioxide laser. $UF_6$ does absorb in the $16\mu$ spectral region, and attempts are continuing in other laboratories to produce a laser in the $16\mu$ region of sufficient power and efficiency to dissociate $UF_6$ in an isotopic selective manner. To date, after investment of very large sums of money, these experiments have been largely unsuccessful.

The proponents of the instant invention have believed, and believe, that the best answer to the uranium isotope separation problem is chemical rather than mechanical. Thus, a number of alternative compounds have been studied, one of the most promising of which is $U(OCH_3)_6$. This compound has a number of absorptions in the $10\mu$ spectral region. One of these is a strong methoxide ligand absorption. The other is a weaker combination band involving uranium oxygen stretching motions which should exhibit isotopic splitting. In initial experiments involving irradiation of $U(OCH_3)_6$ with a variety of laser lines in the P branch of the $10.6\mu$ laser transition, both absorptions appear to contribute to the isotopically selective dissociation process.

SUMMARY OF THE INVENTION

In accordance with the present invention it has been found that upon irradiation of a gaseous $U(OCH_3)_6$ sample with $80\mu$ sec laser pulses on the P(38) $10.6\mu$ $CO_2$ laser transition with a pulse energy of ca. $3J/cm^2$, there is a change in the ratio of mass peaks corresponding to fragments of the parent $^{235}U(OCH_3)_6$ and $^{238}U(OCH_3)_6$ compounds. The changes in mass peaks are measured via signal averaging the mass spectrum on a Hewlett-Packard model mass spectrometer. The data clearly indicate a change in the ratio of the fragment peak attributed to the $^{235}U$ and $^{238}U$ fragments and corresponding enrichment of the sample in $^{235}U$. The enrichment ratio observed in a single pass experiment corresponds to at least 10 times the enrichment in a single pass in a gaseous diffusion plant.

The present invention provides a practical, relatively inexpensive method for uranium isotope enrichment. A principle feature of the present invention is improved one-step syntheses of uranium hexamethoxide and mixed methoxy uranium (VI) fluorides from readily available uranium hexafluoride. An alternative, two-step synthesis from uranium tetrachloride is also described.

GENERAL DESCRIPTION OF THE INVENTION

The enrichment of uranium in the isotope $^{235}U$ via the selective infrared irradiation of the $10.6\mu$ region infrared transitions of $U(OCH_3)_6$ (T. J. Marks and J. H. Coleman, U.S. Pat. No. 4,097,384 [1978] with a pulsed, discretely tunable $CO_2$ infrared gas laser has been demonstrated recently by Miller, DeFord, Marks, and Weitz. (S. S. Miller, D. D. DeFord, T. J. Marks and E. Weitz, *J. Amer. Chem. Soc.*, 101, 1036 [1979]). It is desirable in the practice of the present invention to have a ready means for industrial scale production of $U(OCH_3)_6$.

In accordance with the present invention it has been discovered that uranium hexamethoxide, $U(OCH_3)_6$, can be conveniently prepared by the reaction of $UF_6$ with $M(OCH_3)_x$ (M=an electropositive metal such as Li, Na, K, etc.) or a methoxy silane $R_nSi(OCH_3)_{4-n}$ (R=an organic group). Alternatively, it can be prepared by converting $UCl_4$ into $U(OCH_3)_6^{-2}$ in one step, followed by oxidation. $U(OCH_3)_nF_{6-n}$ compounds can be prepared by reaction of $UF_6$ with $U(OCH_3)_6$ or appropriate quantities of $R_nSi(OCH_3)_{4-n}$.

The high-valent uranium alkoxides are of current interest as organic medium-compatible precursors for new uranium compounds and as subjects for isotopically-selective infrared photochemical studies. Although the hexaalkoxides have been known for some time, the existing syntheses are tedious and inefficient (typically five steps are required for $U(OCH_3)_6$ in the conventional synthesis starting from $UCl_4$; other hexaalkoxides can be prepared from $U(OCH_3)_6$ by transalkoxylation, according to the reaction:

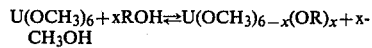

or

where R' and R" are different alkyl groups.

Method A—Synthesis via NaOCH₃

Sodium methoxide, NaOCH₃, was prepared from sodium metal and dry methanol. It was handled under N₂ at all times. In a glove box, a three-neck 500 ml round bottom flask fitted with a serum cap and gas inlet was charged with a magnetic stir bar and 9.0 g (0.17 moles) NaOCH₃. Uranium hexafluoride (9.36g, 0.0266 moles) was sublimed as colorless white crystals into a two-neck 200 ml flask fitted with a greaseless gas inlet connected directly to the vacuum line via an Ultra-Torr connector and maintained at −78° C. Apiezon grease is used on the joints of the flask. After sublimation was completed, the flask was filled with N₂ and a serum cap (previously affixed to an adaptor) was exchanged for the stopper in the flask. Next, 150 ml of dry CH₂Cl₂ was introduced from a CH₂Cl₂ distillation apparatus through a stainless steel cannula under positive nitrogen pressure. Other halogenated hydrocarbons such as CFCl₃ may be used in place of the methylene chloride. The solution was allowed to warm to approximately 0° C., whereby most of the UF₆ dissolved.

Next, 250 ml of CH₂Cl₂ was introduced in like manner to the NaOCH₃ with rapid stirring, with the flask immersed in a dry-ice/acetone slush bath (−78° C.). The NaOCH₃ suspension was brought to −78° C. and the UF₆ solution then immediately transferred via positive nitrogen pressure over a 15-minute period. Reaction ensued rapidly upon addition of UF₆ to form a deep red-brown solution. The reaction mixture was allowed to warm gradually to 0° C. (ca. 1.5 hours), at which time an ice-slush was substituted, and stirring of the deep red solution continued for an additional 1.5 hours at 0° C. to ensure complete reaction. Decomposition of U(OCH₃)₆ over prolonged periods is slight at 0° C.

The solid residue was next removed by filtration under N₂ and the halogenated hydrocarbon solvent removed under vacuum from the resulting clear red filtrate. The red solid was dissolved in 50 ml of hydrocarbon solvent, e.g. dry pentane, the solution refiltered, and the pentane removed under vacuum leaving 4.6 g (42%) of purple-red plates having a melting point, nuclear magnetic resonance spectrum and infrared spectrum identical to an authentic sample. The reaction can also be carried out with other methoxides such as lithium or potassium methoxide, but to no advantage over sodium methoxide.

Method B—Synthesis via Methyltrimethoxysilane

A similar procedure, but using methyltrimethoxysilane (CH₃)Si(OCH₃)₃ in place of NaOCH₃ gave pure U(OCH₃)₆ in 60% yield.

Methyltrimethoxysilane, (CH₃)Si(OCH₃)₃, was freshly prepared from LiOCH₃ and CH₃SiCl₃. It was handled and stored under nitrogen at all times. Methyltrimethoxysilane (1.9 ml, 0.013 mole) was syringed into a nitrogen filled 200 ml round bottom flask fitted with a serum cap, gas inlet, and containing a magentic stir bar. Next, 100 ml of dry CH₂Cl₂ was introduced under positive nitrogen pressure as previously described, and the solution brought to −78° C. in a dry-ice/acetone slush bath.

Uranium hexafluoride (1.86 g, 0.00528 mole) was sublimed into a 200 ml flask as previously described and dissolved in 70 ml CH₂Cl₂. The UF₆ solution was transferred to the silane solution under a positive nitrogen pressure with rapid stirring over a five-minute period. Reaction was immediate, giving a deep red solution.

The reaction mixture was allowed to warm to 0° C. over a one-hour period and then stirred at 0° C. in an ice slush for an additional 1.5 hours. The CH₂Cl₂ was removed under vacuum, 40 ml dry pentane was added to the red residue, and the solution filtered from the remaining solid. The solid was washed with an additional 10 ml aliquot of pentane. The pentane was then removed under vacuum leaving 1.3 g (61%) of purple-red microcrystals characterized as above. In other runs at lower temperatures, yields as high as 72% were achieved. Reactions utilizing (CH₃)₃SiOCH₃ appear to give a less pure, oily product.

Method C—Synthesis via Uranium Tetrachloride and LiOCH₃

A solution of LiOCH₃ was prepared in a 500 ml three-neck flask under nitrogen by dissolving 5.5 g (0.79 moles) Li metal in 150 ml dry methanol. To this solution was added 50 g (0.13 mole) uranium tetrachloride and the mixture was stirred for one hour at room temperature. Next, the methanol was distilled off and the resulting light green Li₂U(OCH₃)₆ powder suspended in 300 ml freshly distilled tetrahydrofuran. With vigorous stirring at 0° C., 58.3 g (0.13 mole) lead tetraacetate was then added in portions. The reaction mixture rapidly turned dark red. It was allowed to warm to room temperature, stirred for one hour, and suction-filtered under nitrogen. Next the solvent was removed under vacuum from the red filtrate and the resulting red solid U(OCH₃)₆ recrystallized from pentane as described in Method A. The yield of U(OCH₃)₆ was 28 g (51%).

This reaction can also be carried out with other methoxides such as sodium or potassium methoxide, but to no advantage over lithium methoxide. Other oxidants such as benzoylperoxide and ozone can be employed, but to no advantage over lead tetraacetate.

The reaction of UF₆ with six equivalents of methanol does not yield U(OCH₃)₆; the reaction with one equivalent is known to give the highly unstable U(OCH₃)F₅.

Compounds of the type U(OCH₃)$_n$F$_{6-n}$ are accessible by the reaction of UF₆ with the appropriate quantity of U(OCH₃)₆ or (CH₃)₃SiOCH₃ at −78° C. The thermal stabilities of the other members of the U(OCH₃)$_n$F$_{6-n}$ series decrease with decreasing n. All of these compounds have been characterized by ¹H or ¹⁹F Fourier transform NMR spectroscopy.

Additionally, with the U(OCH₃)₆ in hand, any other uranium hexaalkoxide is accessible by reacting U(OCH₃)₆ with an excess of the appropriate alcohol and driving off the methanol (transalkoxylation). The equilibrium

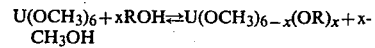

$$U(OCH_3)_6 + xROH \rightleftharpoons U(OCH_3)_{6-x}(OR)_x + xCH_3OH$$

where x=0–6 can be shifted by distilling out the methanol or absorbing it in molecular sieves.

We claim:

1. A process for synthesizing uranium hexamethoxide by reacting uranium hexafluoride with a methoxide having formula M(OCH₃)$_x$ wherein M is an electropositive metal of group 1A of the periodic table and x is 1, or M is a silicon residue having 1 to 3 alkyl radicals, and x is an integer from 1 to 3 said method comprising the steps of:
dissolving UF₆ in a dry halogenated hydrocarbon solvent selected from the group consisting of chlorinated aliphatic solvents, chlorofluorinated aliphatic solvents and mixtures thereof cooled to below 0° C., suspending said methoxide in a dry halogenated hydrocarbon solvent selected form the group consisting of chlorinated aliphatic solvents, chlorofluorinated aliphatic solvents and mixtures thereof cooled to below 0° C., preparing a reaction mixture by gradually adding the solution of $UF_6$ to the suspension of said methoxide and allowing said reaction mixture gradually to warm up to a temperature of about 0° C., separating a red solid reaction product from said halogenated hydrocarbon solvent, and washing said reaction product with a dry hydrocarbon solvent to provide a purified uranium hexamethoxide.

2. The process as set forth in claim 1 wherein said halogenated hydrocarbon solvent is $CH_2Cl_2$ and wherein said hydrocarbon solvent is pentane.

3. The process as set forth in claim 1 wherein said halogenated hydrocarbon solvent is $CFCl_3$.

* * * * *